United States Patent
Locke et al.

(10) Patent No.: US 10,092,682 B2
(45) Date of Patent: Oct. 9, 2018

(54) EXPANDABLE FLUID COLLECTION CANISTER

(71) Applicant: KCI Licensing, Inc., San Antonio, TX (US)

(72) Inventors: Christopher Brian Locke, Bournemouth (GB); Gareth Stephenson, Southampton (GB)

(73) Assignee: KCI Licensing, Inc., San Antonio, TX (US)

( * ) Notice: Subject to any disclaimer, the term of this patent is extended or adjusted under 35 U.S.C. 154(b) by 580 days.

(21) Appl. No.: 14/162,432

(22) Filed: Jan. 23, 2014

(65) Prior Publication Data
US 2014/0276499 A1   Sep. 18, 2014

Related U.S. Application Data

(60) Provisional application No. 61/780,143, filed on Mar. 13, 2013.

(51) Int. Cl.
*A61M 1/00* (2006.01)
*A61F 13/02* (2006.01)

(52) U.S. Cl.
CPC ....... *A61M 1/0088* (2013.01); *A61F 13/0216* (2013.01); *A61F 13/0223* (2013.01); *A61M 1/0015* (2014.02); *A61M 1/0001* (2013.01)

(58) Field of Classification Search
CPC combination set(s) only.
See application file for complete search history.

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 A1 | 3/1986 |
| AU | 745271 | 4/1999 |

(Continued)

OTHER PUBLICATIONS

N. A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).

(Continued)

*Primary Examiner* — Tatyana Zalukaeva
*Assistant Examiner* — Guy K Townsend

(57) ABSTRACT

A bodily fluid collection system includes a reduced pressure treatment unit for providing reduced pressure to a fluid collection system through a canister having a container with an inlet adapted to be fluidly coupled to the fluid collection system, an outlet adapted to be connected to a source of reduced pressure, and an absorptive lamination disposed within the container. The absorptive lamination may be formed from a plurality of absorptive layers and wicking layers interleaved between the absorptive layers that collectively manifold bodily fluids from a tissue site into and throughout the absorptive lamination to trap and collect the bodily fluids. The container expands as the absorptive lamination swells with the bodily fluid being collected.

15 Claims, 5 Drawing Sheets

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,136,696 A * | 1/1979 | Nehring | A61M 1/0011 604/142 |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielson | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Cation | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,630,855 A | 5/1997 | Lundback | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,520,872 B2 * | 4/2009 | Biggie | A61M 1/0088 601/6 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2006/0079852 A1 | 4/2006 | Bubb et al. | |
| 2008/0082059 A1* | 4/2008 | Fink | A61M 1/0001 604/305 |
| 2008/0200905 A1* | 8/2008 | Heaton | A61M 1/0011 604/543 |
| 2009/0292263 A1* | 11/2009 | Hudspeth | A61M 1/0001 604/313 |
| 2009/0306630 A1* | 12/2009 | Locke | A61M 1/0001 604/543 |
| 2011/0172616 A1* | 7/2011 | Hartwell | A61M 1/0001 604/319 |
| 2011/0257613 A1* | 10/2011 | Locke | A61F 13/02 604/319 |
| 2013/0032539 A1* | 2/2013 | Bonhomme | B01D 61/18 210/650 |
| 2013/0053797 A1 | 2/2013 | Locke | |
| 2013/0270166 A1* | 10/2013 | Locke | B01D 19/0036 210/188 |
| 2014/0276499 A1* | 9/2014 | Locke | A61M 1/0015 604/322 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| DE | 10 2010 060543 | 4/2012 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/010424 | 9/1990 |
| WO | 93/09727 | 5/1993 |

(56) References Cited

FOREIGN PATENT DOCUMENTS

| WO | 94/020041 | 9/1994 |
|---|---|---|
| WO | 96/05873 | 2/1996 |
| WO | 97/18007 | 5/1997 |
| WO | 99/13793 | 3/1999 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), vol. 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, p. 1.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., vol. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovic, V. Ðukić, Ž. Maksimović, Ð. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, "An Improved Sump Drain-Irrigation Device of Simple Construction," Archives of Surgery 105 (1972) pp. 511-513.

C.E. Tennant, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians (Jul. 2007).

International Search Report corresponding to PCT, dated May 13, 2014.

* cited by examiner

EXPANDABLE FLUID COLLECTION CANISTER

The present invention claims the benefit, under 35 USC § 119(e), of the filing of U.S. Provisional Patent Application Ser. No. 61/780,143, entitled "EXPANDABLE FLUID COLLECTION CANISTER," filed Mar. 13, 2013, which is incorporated herein by reference for all purposes.

TECHNICAL FIELD

The present invention relates generally to tissue treatment systems and in particular to systems and methods for collecting bodily fluid.

BACKGROUND

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formulation of granulation tissue. Typically, reduced pressure is applied to tissue through a porous pad or other manifold device. The porous pad contains cells or pores that are capable of distributing reduced pressure to the tissue and channeling fluids that are drawn from the tissue. The porous pad often is incorporated into a dressing having other components that facilitate treatment.

Wound fluids or exudates are generally collected in a canister for disposal or analysis. Wound fluid primarily comprises plasma in addition to red and white blood cells, platelets, bacteria, and a variety of proteinaceous material. Plasma consists primarily of saline. In clinical practice, canisters should be sized appropriately to obviate the need for frequent replacement even when used in the treatment of patients with wounds generating a high volume of exudate. Conversely, canisters should not be bulky so as to fill care facilities' storage spaces or consume unnecessary resources for hazardous waste disposal of canisters filled with potentially infectious bodily fluid.

SUMMARY

In one illustrative embodiment, a bodily fluid canister comprises an inlet, an outlet, a container, and a plurality of layers of absorptive material and a plurality of layers of wicking material contained within the container. The plurality of layers of wicking material may be situated proximate to the plurality of layers of absorptive material. The plurality of layers of wicking material may be oriented in an alternating pattern with the plurality of layers of absorptive material such that each layer of absorptive material is proximate to at least one layer of manifold material. The plurality of layers of wicking material and the plurality of layers of absorptive material may be oriented essentially vertically with the container.

In another illustrative embodiment, a bodily fluid canister is provided for use with a reduced pressure treatment system. The bodily fluid canister comprises an inlet, an outlet, liquid impervious container, and a plurality of layers of absorptive material and a plurality of layers of wicking material contained within the container. The inlet may be disposed in the container, the inlet adapted to be fluidly connected to a tissue site. The reduced pressure treatment system may include a porous pad positioned proximate to a tissue site. An outlet may be disposed in the container and is adapted to be fluidly connected to a reduced pressure source. A plurality of layers of wicking material and a plurality of layers of absorptive material may be positioned within the container. The plurality of layers of wicking material and the plurality of layers of absorptive material may be positioned proximate to one another and each of the plurality of layers of absorptive material may be positioned proximate to at least one of the plurality of layers of manifold material. The plurality of layer of wicking material and the plurality of layers of absorptive material may be oriented essentially vertically within the container. The container may be configured to be volumetrically expandable.

In still another embodiment, a method for volumetrically expanding a bodily fluid canister is provided. The method comprises introducing bodily fluid into a canister, the canister comprising a container containing a plurality of layers of absorptive material within the canister adapted to attract and retain bodily fluid and a plurality of layers of wicking material within the canister adapted to distribute bodily fluid along the plurality of layers of absorptive material. The method further comprises volumetrically expanding the canister, the canister configured to expand upon bodily fluid distribution to the plurality of layers of wicking material and the plurality of layers of absorptive material.

In yet another embodiment, a canister for collecting bodily fluids from a fluid collection system for delivering reduced pressure to a tissue site from a source of reduced pressure is disclosed. The canister may comprise a container having a chamber being expandable to receive and collect bodily fluids from the tissue site in response to the application of the reduced pressure, an inlet fluidly coupled to the chamber of the container and configured to be in fluid communication with the fluid collection system for delivering the bodily fluids into the chamber of the container, and an outlet fluidly coupled to the chamber of the container and configured to be in fluid communication with the source of reduced pressure for providing reduced pressure through the chamber of the container to the fluid collection system. The canister may further comprise an absorptive lamination disposed within the container and adapted to trap and collect a liquid portion of the bodily fluids separated from the gaseous portion of the bodily fluids flowing from the inlet to the outlet within the container, wherein the container expands as the absorptive lamination swells to absorb the liquid portion of the bodily fluids. The absorptive lamination may comprise a plurality of absorptive layers and a plurality of wicking layers interleaved between the absorptive layers.

Other objects, features, and advantages of the illustrative embodiments will become apparent with reference to the drawings and detailed description that follow.

DETAILED DESCRIPTION OF ILLUSTRATIVE EMBODIMENTS

In the following detailed description of several illustrative embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure associated with tissue at the tissue site. Although the terms "vacuum" and "negative pressure" may be used to describe the pressure applied to the tissue site, the actual pressure reduction applied to the tissue site may be significantly less than the pressure reduction normally associated with a complete vacuum. Reduced pressure may initially generate fluid flow in the area of the tissue site. As the hydrostatic pressure around the tissue site approaches the desired reduced pressure, the flow may subside, and the reduced pressure is then maintained. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

The term "tissue site" as used herein refers to a wound or defect located on or within any tissue, including but not limited to, bone tissue, adipose tissue, muscle tissue, neural tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location.

Figure 1:
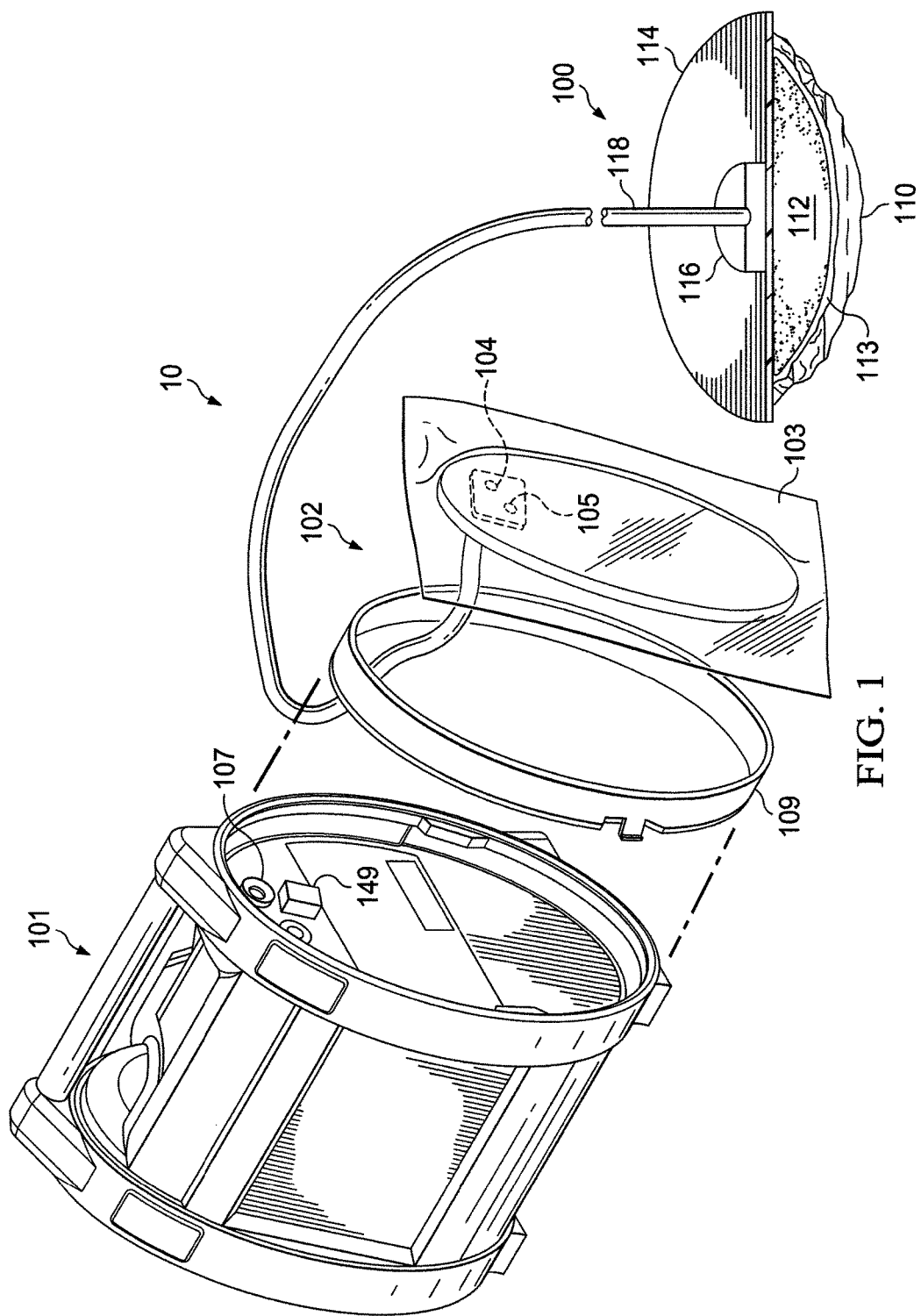
FIG. 1 shows a perspective view of a bodily fluid collection system comprising a reduced pressure treatment unit for providing reduced pressure to a fluid collection system through a first embodiment of a canister including a container having absorptive layers with interleaving wicking layers disposed in the container according to an illustrative embodiment.
Figure 2:
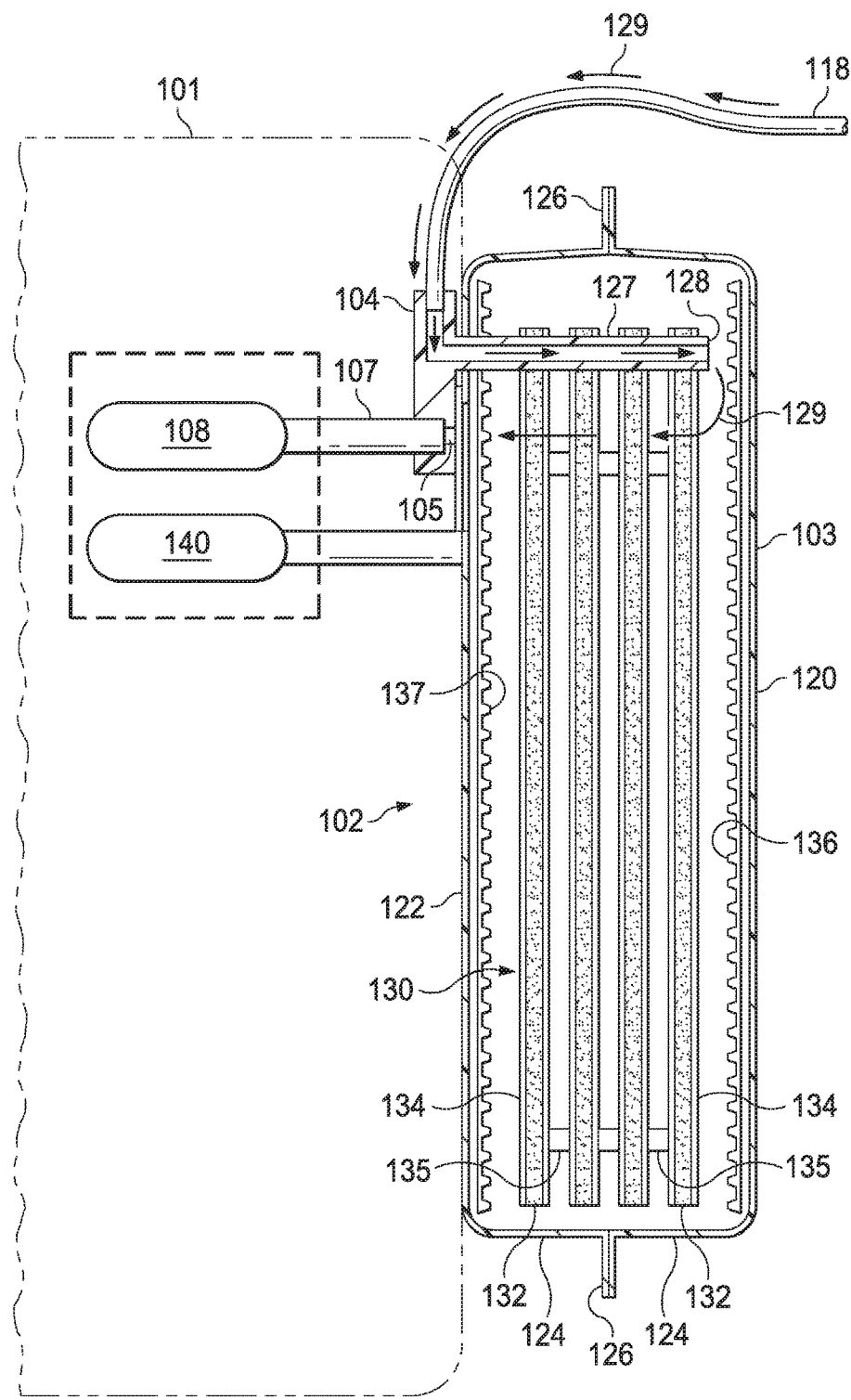
FIG. 2 shows an exploded, cross-sectional view of the canister and a partially schematic cross-sectional view of the reduced pressure treatment unit comprising components of the bodily fluid collection system of FIG. 1.

Referring to FIGS. 1 and 2, a reduced pressure treatment system 10 comprises a fluid collection system 100 for applying reduced pressure therapy to a patient, a reduced pressure treatment unit 101 for providing the reduced pressure, and a canister 102 fluidly coupled between the fluid collection system 100 and the reduced pressure treatment unit 101 for collecting fluids from a patient according to one illustrative embodiment. The canister 102 comprises a container 103 having a chamber, an inlet 104 being a coupling for providing fluid communication into the chamber of the container 103, and an outlet 105 being a coupling for providing fluid communication out from the chamber of the container 103. The inlet 104 is adapted to be fluidly coupled to the fluid collection system 100 for providing reduced pressure to the fluid collection system 100 and receiving bodily fluids from the patient. The outlet 105 is adapted to be connected to a reduced pressure port 107 of the reduced pressure treatment unit 101 to provide reduced pressure to the fluid collection system 100 from a reduced pressure source 108 that may be contained within the reduced pressure treatment unit 101. The inlet 104 and the outlet 105 are preferably disposed at one end of the container 103 so that both may be positioned at a higher elevation relative to the other end of the container 103 when the canister 102 is utilized in operation. The canister 102 may further comprise a support member such as, for example, a carrier ring 109 that may be releasably connected to the reduced pressure treatment unit 101 to hold the container 103 in place during operation of the reduced pressure treatment unit 101.

The fluid collection system 100 is adapted to be positioned proximate a tissue site 110 of a patient for delivering reduced pressure to the tissue site 110 and collecting bodily fluids from the tissue site 110. The fluid collection system 100 comprises a manifold 112 in fluid communication with the tissue site 110 and a drape 114 adapted to cover the manifold 112 for providing a substantially airtight seal over the tissue site 110. The fluid collection system 100 may further comprise a connector 116 fluidly coupled to the manifold 112 through the drape 114 and a conduit or tube 118 containing at least one lumen for the transmission of fluids, both gaseous and liquid. The tube 118 is adapted to be fluidly coupled between the connector 116 and the inlet 104 of the canister 102 for transmitting fluids between the canister 102 and the tissue site 110.

The manifold 112 may be a bioabsorbable or bioinert material capable of distributing reduced pressure at various desired levels. The drape 114 may include an adhesive seal (not shown) that not only maintains the reduced pressure at various levels, but also holds the fluid collection system 100 in place over the tissue site 110. The manifold 112 may be a bioabsorbable or bioinert material capable of distributing reduced pressure to the tissue site 110. In one embodiment, the manifold 112 may be an open cell, reticulated foam comprising, for example, a polyurethane material. The wound dressing 112 delivers reduced pressure to the tissue site 110 to provide therapeutic treatment to the tissue site 110 and allows exudates and bodily fluids to flow from the tissue site 110 to the canister 102 where the exudates and bodily fluids are collected.

The reduced pressure treatment unit 101 may comprise the reduced pressure source 108 as described above. The reduced pressure source 108 may be, for example, a vacuum pump driven by a motor. In another embodiment, reduced pressure may be provided by a manually-actuated pump such as a compressible bellows pump. In still another embodiment, the reduced pressure may be provided by a wall suction port either with or without a separate pressure regulator. The reduced pressure treatment unit 101 may also comprise a processing unit (not shown) for controlling various features of the reduced pressure treatment unit 101 such as, for example, the level and timing of the reduced pressure being applied to the tissue site 110. The reduced pressure treatment unit 101 may further comprise other equipment such as, for example, a source of positive pressure.

The container 103 may be constructed of a liquid impervious material such as, for example, a thermoplastic material such as polyurethane to contain the exudates and bodily fluids collected from the tissue site 110. The chamber of the container 103 may have a volume that is preferably variable to accommodate the collection of exudates and bodily fluids from the tissue site 110 expanding from an empty state to a full state after collecting such fluids. In one embodiment, the container 103 may comprise a flexible bag having walls that are elastic and expandable as needed to accommodate the collection of exudates and bodily fluids. In another embodiment, the flexible bag may have walls that are less elastic or inelastic but nonetheless collapsible in the empty state and expandable to the full state as needed to accommodate the collection of exudates and bodily fluids. In one embodiment, the container 103 may comprise a flexible bag formed from a single tubular sheet of film sealed at both ends. In another embodiment, the container 103 may comprise a flexible bag formed from two sheets of film sealed around the edges and shown more specifically in FIG. 1 which shows the chamber having an oval shape. The chamber of the container 103 may have a circular or rectangular shape (e.g., see the chamber of container 303 in FIG. 3) as necessary to accommodate the structure and fluidics of the system.

In yet another embodiment, the container 103 may comprise two walls joined around the edges by a connecting member that provides expandability of the chamber of the container 103. Referring more specifically to FIG. 2, the container 103 may comprise a first wall 120, a second wall 122, and a connecting member 124, wherein the perimeters of the first wall 120 and the second wall 122 are joined together by the connecting member 124. The first wall 120, the second wall 122, and the connecting member 124 define the chamber of the container 103 that may accommodate the exudates and bodily fluids as they are collected from the tissue site 110. In one embodiment, the connecting member 124 may comprise one or more pleats 126 that allow the chamber of the container 103 to expand from the empty state to the filled state. In another embodiment, the connecting member 124 may comprise a material with elastic characteristics. In yet another embodiment, the connecting member 124 may be configured as a Z-fold to permit expansion of the chamber of the container 103. Other configurations of the container 103 may provide similar volumetric expandability of the chamber.

As indicated above, the inlet 104 and the outlet 105 are preferably disposed at one end of the container 103 so that both may be positioned at a higher elevation relative to the other end of the container 103 when the canister 102 is utilized in operation. Thus, the container 103 may be oriented more vertically with the inlet 104 and the outlet 105 being elevated to utilize gravity to facilitate filling the chamber of the container 103 with the exudates and bodily fluids being collected. In one embodiment, the container 103 may contain an absorptive material such as a foam, hydrogel, or a water-swelling polymer for collecting and treating the exudates and bodily fluids being collected from the tissue site 110. In such embodiments, it is also desirable that the exudates and bodily fluids enter the chamber of the container 103 on the distal side of the container 103 adjacent the first wall 120 allowing the absorptive material to trap and collect the liquid fluids while the gaseous fluids exit the chamber of the container 103 on the proximal side of the container 103 adjacent the second wall 122. Thus, the inlet 104 and the outlet 105 may be disposed on opposing walls of the container 103. In another embodiment as more specifically shown in the figures, the inlet 104 and the outlet 105 may both be disposed on the proximal side of the container 103 through the second wall 122 wherein the inlet 104 is in fluid communication with a tube 127 having a distal end 128 extending within the chamber to the distal side of the container 103 adjacent the first wall 120 so that the absorptive material better traps and collects the liquid fluids while the gaseous fluids exit the chamber of the container 103 through the outlet 105 as illustrated by arrows 129 representing the flow of the fluids.

When the container 103 is filled with an absorptive material in bulk volume, the absorbent material often failed to expand or inflate the container 103 to completely fill the chamber of the container 103 with the exudates and bodily fluids being collected from the tissue site 110. Moreover, the absorptive material tended to saturate in localized areas without absorbing the fluids throughout the entire volume of the absorptive material. Even when the container 103 and the absorptive material within the container 103 were oriented vertically, the vertical orientation exacerbated the localized saturation condition. It is desirable to overcome these problems so that the container 103 would be completely filled to reduce the expense associated with utilizing additional containers and reduce the maintenance required by the patient or a caregiver.

These problems are overcome by disposing individual layers of absorptive material within the container 103 wherein the absorptive layers are spaced apart from one another that may form an absorptive lamination to enhance the collection and flow of fluids throughout the entire volume of the absorptive lamination. These problems are further overcome by interleaving layers of wicking material within the space between the absorptive layers to further enhance the flow of fluids between the absorptive layers and throughout the entire volume of the absorptive lamination. Using such an absorptive lamination including wicking layers interleaved between the absorptive layers within the container 103 greatly enhances the ability of the container 103 to expand and completely fill to overcome these problems and do so regardless of orientation. When the container 103 contains an absorptive lamination as just described, the absorptive capabilities of the container 103 are still enhanced when the container is oriented in a horizontal position as opposed to a vertical position.

Referring more specifically to FIG. 2, one exemplary embodiment of an absorptive lamination 130 is shown and comprises a plurality of absorptive layers 132 of absorptive material that are spaced apart from each other as described above. The absorptive layers 132 may be spaced apart from each other by spacers (not shown) or any other means to maintain the spaced apart relationship between the absorptive layers 132 when subjected to a reduced pressure during operation of the reduced pressure treatment unit 101. The absorptive lamination 130 contains a plurality of wicking layers 134 of wicking material disposed between the absorptive layers 132. In one embodiment, one wicking layer 134 may be disposed or interleaved between each absorptive layer 132 as described above but not shown. In another embodiment, one wicking layer 134 may be disposed proximate each side of one of the absorptive layers 132 such that a pair of wicking layers 134 may be associated with each absorptive layer 132 as shown. In this embodiment, the absorptive lamination 130 may further comprise spacers 135 disposed between each pair of wicking layers 134 to provide further spacing between the absorptive layers 132. The absorptive lamination 130 may be oriented within the chamber of the container 103 so that the absorptive layers 132 and the wicking layers 134 are substantially parallel to the first wall 120 and the second wall 122 of the container 103. These embodiments enhance the distribution of bodily fluids to the absorptive layers 132 throughout the entire chamber of the container 103 to enhance the fluid storage capability of the absorptive lamination 130.

The wicking layers 134 may comprise a wicking material having flow channels that support the flow of fluids at least through the width of each wicking layer 134, i.e., generally perpendicular to the length or longitudinal axis of the wicking layer 134. The flow channels of the wicking material are capable of supporting the flow of fluids even when under reduced pressure being applied within the container 103. The wicking material may be a non-woven material such as, for example, Libeltex TDL2 available from LIBEL-TEX bvba located in Belgium, or a reticulated open-cell polyurethane foam. The absorptive layers 132 may comprise, for example, a textile substrate (e.g., woven or knit fabrics), a foam, a hydrogel, a hydrocolloid, a superabsorbent polymer (e.g., Texsus CCBSL 13OLL available from Texsus Spa located in Italy), a silica gel, a water swelling polymer, a polysaccharide (e.g., chitosan, carboxymethylcellulose, hydroxylmethylcellulose, hyaluronic acid, alginate, pectin, etc.), proteinaceous material (glycoprotein, gelatin, etc.), and combinations thereof.

The wicking layers 134 and the absorptive layers 132 of may each further comprise an antimicrobial agent and thus be adapted to have antimicrobial properties to effect a bioburden log reduction of greater than one or, more preferably, greater than three. By way of a non-limiting example, this antimicrobial property may be accomplished by adding ionic silver to the wicking material of the wicking layers 134 or the absorptive material of the absorptive layers 132. The wicking layers 134 and the absorptive layers 132 of may each further comprise other chemicals or agents to facilitate the collection and storage of exudates and bodily fluids from the tissue site 110.

The canister 102 may further comprise a first textured layer 136 contained within the container 103 adjacent to the first wall 120 and a second textured layer 137 contained within the container 103 adjacent to the second wall 122. The first textured layer 136 and the second textured layer 137 may be constructed from a fluid impermeable material. The first textured layer 136 and the second textured layer 137 may each be a sheet of material having a textured side that is corrugated or comprises a plurality of protrusions or projections extending into the chamber of the container 103 and facing the absorptive lamination 130. The textured sides of the first textured layer 136 and the second textured layer 137 may have other shapes resulting from being channeled, creased, folded, grooved, indented, pleated, or ribbed. When the chamber of the container 103 subjected to a reduced pressure, the first textured layer 136 and the second textured layer 137 collapse against the sides of the absorptive lamination 130. The first textured layer 136 and the second textured layer 137 may provide a fluid reservoir for a bolus of bodily fluid entering the container 103, allowing the bodily fluid from the tissue site 110 to be distributed more thoroughly across the face of the absorptive lamination 130 to enhance the ability of the absorptive layers 132 collect and store such fluids. Additionally, textured surfaces of the first textured layer 136 and the second textured layer 137 provide additional spacing adjacent the outermost absorptive layers 132 and/or the wicking layers 134 to further enhance the flow of bodily fluids throughout the entire absorptive lamination 130.

The absorptive layers 132 and the wicking layers 134 may be organized in other alternating sequences of absorptive material and wicking material. Additionally, the absorptive layers 132 and the wicking layers 134 may be formed into a composite rather than being discrete layers of material. For example, an absorptive composite may be formed from co-extruding absorptive material and wicking material such that the absorptive composite possesses characteristics similar to the characteristics of the discrete absorptive layers 132 and the wicking layers 134. The absorptive and wicking lamina of the absorptive composite would then be aligned in an alternating sequence when disposed within the container 103.

Figure 2A:
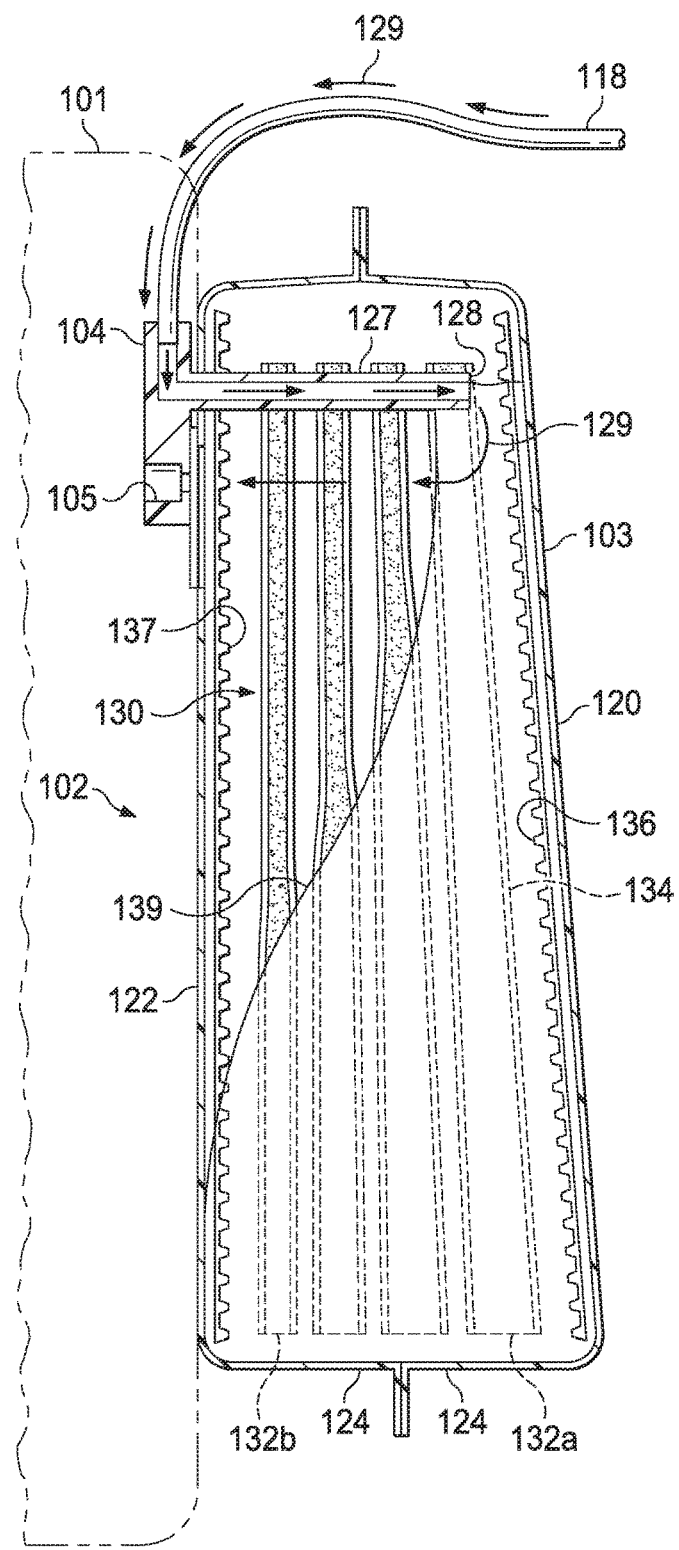
FIG. 2A shows the canister of FIG. 2 with the container partially filled with bodily fluids drawn from the fluid collection system.
Figure 2B:
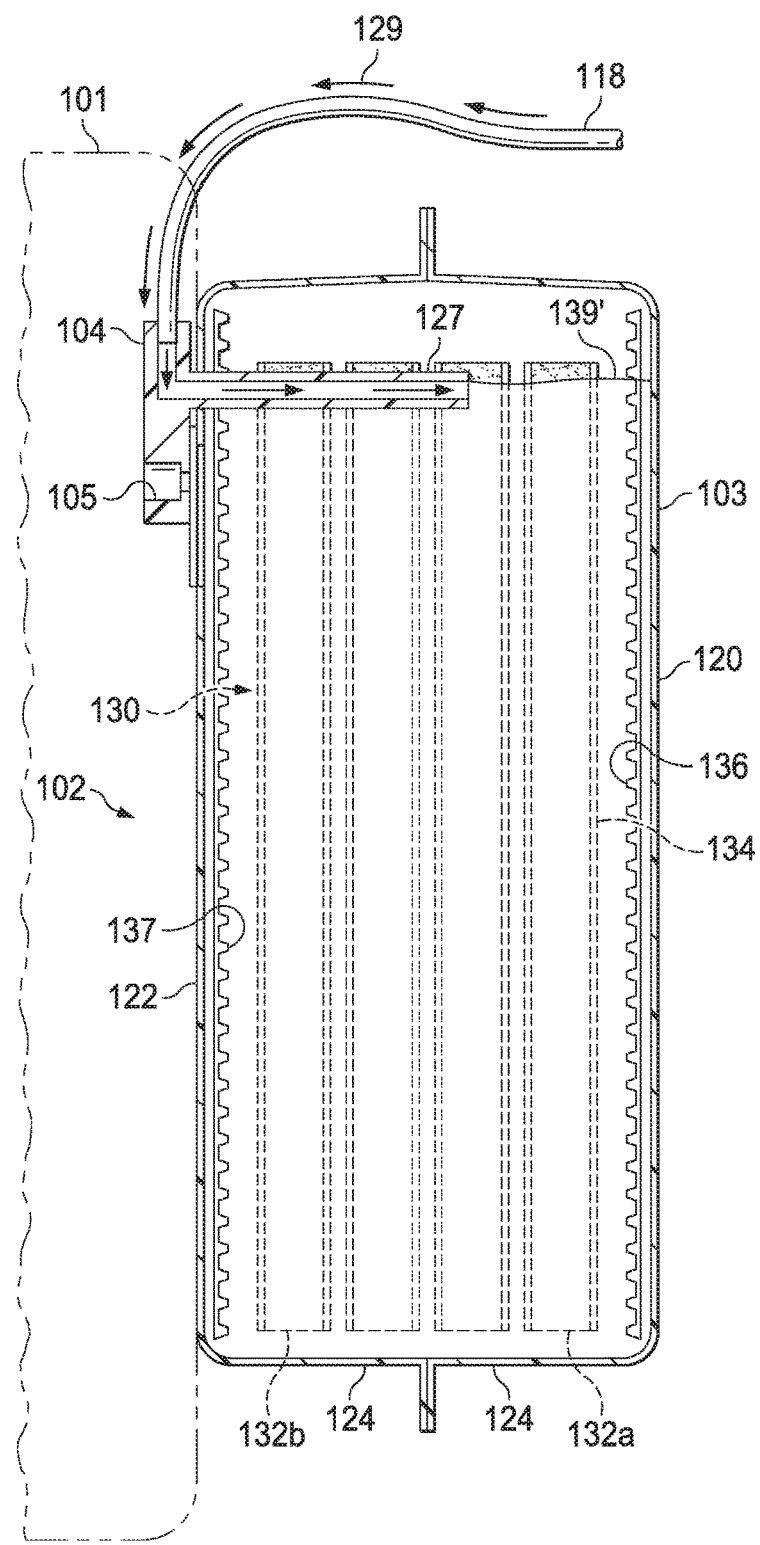
FIG. 2B shows the canister of FIG. 2 with the container completely filled with bodily fluids drawn from the fluid collection system.

In operation, the absorptive lamination 130 including wicking layers interleaved between the absorptive layers within the container 103 greatly enhances the ability of the container 103 to expand and completely fill the chamber as described above, especially when oriented in a generally vertical position. Referring more specifically to FIGS. 2, 2A, and 2B, the container 102 of the canister 102 is shown as being substantially vertically oriented and expanding from an empty state to being partially filled and then completely filled, respectively. Referring to FIG. 2A, the container 102 is shown as being partially filled with bodily fluids and expanding at the lower end near the bottom of the container 102. The bodily fluids and exudates are drawn from the tissue site 110 into the inlet 104 and the tube 127, and then flow into the chamber of the container 102 through the distal end 128 of the tube 127. When the bodily fluids enter the chamber of the container 102, they begin to separate into gaseous and liquid components with the gaseous fluids exiting the outlet 105 as indicated by the arrows 129 and the liquid fluids manifolding down the side of the absorptive lamination 130 with the assistance of gravity as indicated by liquid line 139. The liquid bodily fluids are manifolded through a combination of the wicking action created by the wicking layers 134 and the osmotic pressure of the absorptive layers 132, and supplemented by the effects of gravity which pulls the fluid downward toward the bottom of the container 102 which begins to expand along with the expanding absorptive layers 132. This leaves the top of the container 102 generally unobstructed by the liquid fluids to manifold the reduced pressure through the tube 127 to the outlet 105. This action also facilitates fluid flow by pulling intermittent bolus' of liquid fluids and exudates from the tissue site 110 down to the bottom of the container 102 by gravity where the absorbent layers 132 have more time to trap and retain the liquid fluids.

As can be seen in the illustration, the absorptive layers 132 continue to expand as the wicking layers 132 continue to channel the liquid fluids across the surfaces of the absorptive layers 132 and the longer the absorptive layers 132 are submersed in the liquid fluids. For example, the most distal absorptive layer 132a has expanded more at the lower end which has expanded more than the lower end of the most proximal absorptive layer 132b with varying degrees of absorption and expansion for each intervening absorptive layer 132. As the container 102 continues to fill with the liquid fluids, the absorptive layers 132 continue to expand until they reach a full capacity such that the container 102 is fully expanded in a filled state as shown in FIG. 2B. When the chamber of the container 102 is substantially filled, the liquid fluid eventually covers the distal end 128 of the tube 127 as shown by fluid line 139' which substantially prevents the continuing flow of bodily fluids from the tissue site 110. The container 102 is capable of expanding with the expansion of the absorptive lamination 132 by means of any of the embodiments described above. It should be understood that the container 102 will function in a substantially horizontal position by virtue of the wicking action provided by the wicking layers 134 without the aid of gravity as long as the distal end 128 of the tube 127 is in an elevated position.

Figure 3:
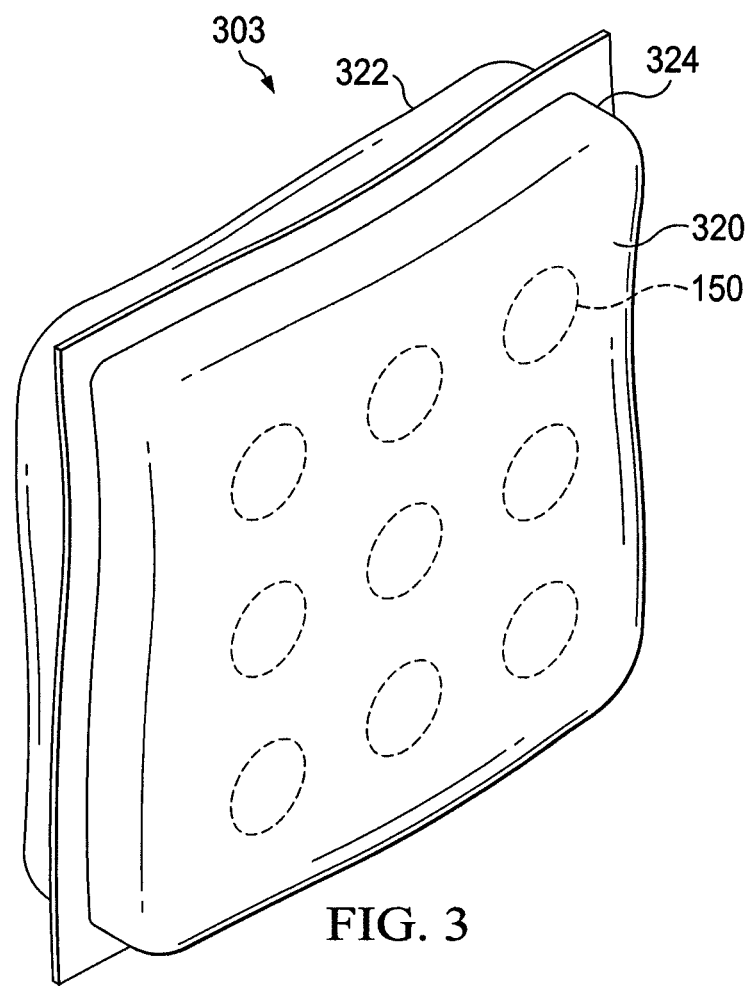
FIG. 3 shows a perspective view of a second embodiment of a container for collecting bodily fluids in the bodily fluid collection system of FIG. 1.

Referring now to FIG. 3, a container 303 is shown is substantially similar in all respects to the container 103 of FIGS. 1 and 2 except for the shape as pointed out above. The container 303 also comprises a first wall 320 and a second wall 322 joined together by the connecting member 324. As also described above, the container 303 may be constructed of a liquid impervious material such as, for example, a thermoplastic such as polyurethane. In one exemplary embodiment, the first wall 320 and the second wall 322 of the container 303 may be constructed of polyurethane film having a cross-sectional thickness greater than about 50 µm wherein the container 303 is substantially impervious to vapor. In another exemplary embodiment, the first wall 320 and a second wall 322 of the container 303 may comprise a material permeable to vapor such as, for example, the same polyurethane film wherein the polyurethane film has a cross-sectional thickness less than about 50 µm but greater than about 15 µm. If the container 303 is permeable to vapor, the reduced pressure treatment unit 101 may further comprise a positive pressure source 140 that may provide positive pressure to the container 303 to facilitate the evaporation of collected bodily fluid into vapor and the subsequent transmission of vapor through the container 303 and into the atmosphere. In one embodiment, the source of positive pressure 140 may be the exhaust of the source negative pressure 108. In another embodiment, the positive pressure source 140 may be activated when the negative pressure source 108 is deactivated.

In yet another exemplary embodiment, the first wall 320 and the second wall 322 of the container 303 may be substantially impervious to vapor but may further comprise portions or regions 150 having a cross-sectional thickness greater than about 5 µm and less than about 50 µm that are permeable to vapor. The regions 150 of vapor permeability allow bodily fluid collected in the container 303 to evaporate into the atmosphere as described above and further assisted by providing positive pressure to the chamber of the container 303. The regions 150 may have varying shapes such as, for example, the shape of a regular polygon or an ellipse. The regions 150 may comprise between about 5% and about 95% of the surface area of the container 303.

In yet another embodiment, a method for collecting bodily fluid from a tissue site is provided. The method comprises disposing a plurality of absorptive layers with wicking layers interleaved between the absorptive layers into a container of a bodily fluid canister, fluidly coupling the container to both a source of bodily fluid and a source of negative pressure, and applying negative pressure through the container to the source of bodily fluid. The method further comprises utilizing the negative pressure to draw the bodily fluids from the tissue site and manifold the bodily fluids to the absorptive layers to collect and trap the liquid portion of the bodily fluids, and allowing the container to volumetrically expand as the absorptive layers swell in size, whereby the container expands to a full state after the absorptive layers are fully absorbed with the liquid fluids.

It will be appreciated that the illustrative embodiments described herein may be used with reduced pressure treatment systems of any type, shape, or size and similarly with canisters of any type, shape, or size. The location of the inlet, outlet, semi-permeable membrane, and flexible bag may also vary depending upon the particular collection system design. Similarly, the geometry of the semi-permeable membrane may be modified as necessary to conform to the contours or configuration of the canister. Similarly, the location of the means to withdraw the collected absorbent may also vary depending upon the particular collection system design.

It should be apparent from the foregoing that an invention having significant advantages has been provided. While the invention is shown in only a few of its forms, it is not just limited but is susceptible to various changes and modifications without departing from the spirit thereof.

We claim:

1. A canister for collecting bodily fluids from a fluid collection system for delivering reduced pressure to a tissue site from a source of reduced pressure, the canister comprising:
   a container having a chamber being expandable to receive and collect bodily fluids from the tissue site in response to an application of the reduced pressure;
   an inlet fluidly coupled to the chamber of the container and configured to be in fluid communication with the fluid collection system for delivering the bodily fluids into the chamber of the container;
   an outlet fluidly coupled to the chamber of the container and configured to be in fluid communication with the source of reduced pressure for providing reduced pressure through the chamber of the container to the fluid collection system;
   an absorptive member comprising absorptive layers and wicking layers positioned on opposing sides of each of the absorptive layers, wherein the wicking layers have flow channels for supporting fluid flow across a surface of the absorptive layers; and
   at least one spacer between the wicking layers of the absorptive member to maintain a space between adjacent wicking layers under reduced pressure.

2. The canister of claim 1, wherein the container comprises a flexible bag having walls formed from an elastic material, and wherein the walls stretch allowing the container to expand as the absorptive member swells.

3. The canister of claim 1, wherein the container comprises a flexible bag having walls formed from a substantially inelastic material, and wherein the walls are collapsible when the container is empty and expandable so that the container expands as the absorptive member swells.

4. The canister of claim 1, wherein the container comprises a first wall and a second wall, and wherein the first wall is joined around edges with the second wall by a connecting member being expandable to allow the container to expand as the absorptive member swells.

5. The canister of claim 4, wherein the connecting member comprises pleats.

6. The canister of claim 4, wherein the connecting member comprises an elastic material.

7. The canister of claim 4, wherein the container comprises an upper end and a lower end, wherein the upper end is adapted to be elevated in operation, and wherein the inlet and the outlet are disposed in the upper end of the container.

8. The canister of claim 7, wherein the inlet and the outlet are disposed on opposing walls of the first wall of the container and the second wall of the container.

9. The canister of claim 7, wherein the inlet and the outlet are disposed on one of the first wall of the container or the second wall of the container, and wherein the canister further comprises a tube fluidly coupled to the inlet and extending into the chamber of the container away from the outlet.

10. The canister of claim 4, wherein the canister further comprises a first textured layer disposed within the container adjacent the first wall of the container.

11. The canister of claim 4, wherein the canister further comprises a second textured layer disposed within the container adjacent the second wall of the container.

12. The canister of claim 1, wherein the container comprises a liquid impermeable material.

13. The canister of claim 1, wherein a first portion of the container comprises a liquid impermeable material and a second portion of the container comprises a vapor permeable material.

14. The canister of claim 1, wherein the absorptive member is an absorptive lamination.

15. The canister of claim 1, wherein a spacer layer comprises the at least one spacer positioned between the wicking layers.

\* \* \* \* \*